(12) United States Patent
Copping et al.

(10) Patent No.: US 8,459,374 B1
(45) Date of Patent: Jun. 11, 2013

(54) EASY OPEN LINERS FOR SOIL SAMPLERS

(76) Inventors: Ceri E B Copping, Badingham (GB);
Lenny Coakley, Newmarket (GB);
Kevin Russell Porter, Longstanton (GB)

( * ) Notice: Subject to any disclaimer, the term of this patent is extended or adjusted under 35 U.S.C. 154(b) by 343 days.

(21) Appl. No.: 12/959,925

(22) Filed: Dec. 3, 2010

(51) Int. Cl.
*G01N 1/04* (2006.01)

(52) U.S. Cl.
USPC .............. 175/20; 175/58; 175/244; 73/864.44

(58) Field of Classification Search
USPC .............................. 175/20, 58, 244; 73/864.44
See application file for complete search history.

(56) References Cited

U.S. PATENT DOCUMENTS

| | | |
|---|---|---|
| 5,606,139 A | 2/1997 | Wittig et al. |
| 2002/0194937 A1 | 12/2002 | Scott et al. |
| 2011/0277566 A1 * | 11/2011 | Merrell et al. ............ 73/864.41 |

FOREIGN PATENT DOCUMENTS

| | | |
|---|---|---|
| GB | 2480290 A | 11/2011 |
| GB | 2480345 A | 11/2011 |
| JP | 9072184 A | 3/1997 |

* cited by examiner

*Primary Examiner* — William P Neuder
(74) *Attorney, Agent, or Firm* — Nancy J. Flint, Attorney At Law, P.A.; Nancy J. Flint, Esq.

(57) ABSTRACT

The invention relates to a system and method for an easy-to-open liner for use in connection with direct push, rotary and coring soil samplers. The liner according to the invention is pre-scored by one or more score lines comprising an indentation of substantially uniform depth or a series of perforations into the outer wall of the liner in one or more locations. The liner of the invention can easily be opened using pliers to expose the sample within the liner without the need of cutting blades or other sharp objects. The liner of the invention permits safe and easy opening in accordance with health and safety requirements.

16 Claims, 4 Drawing Sheets

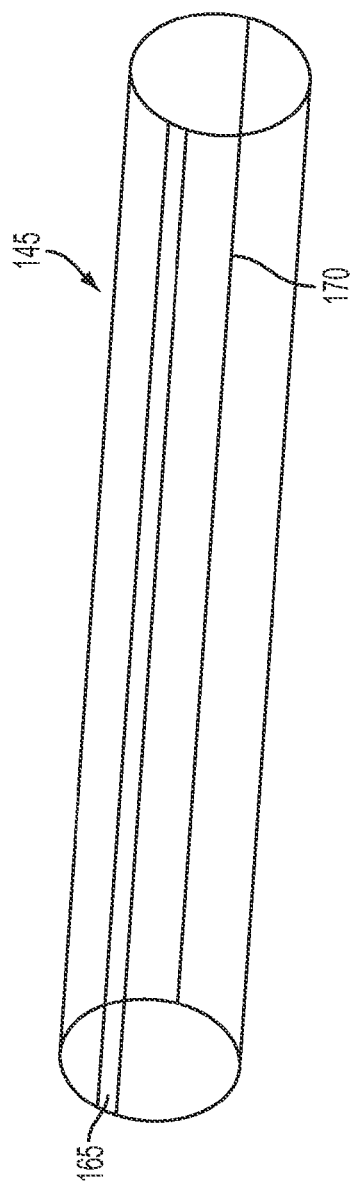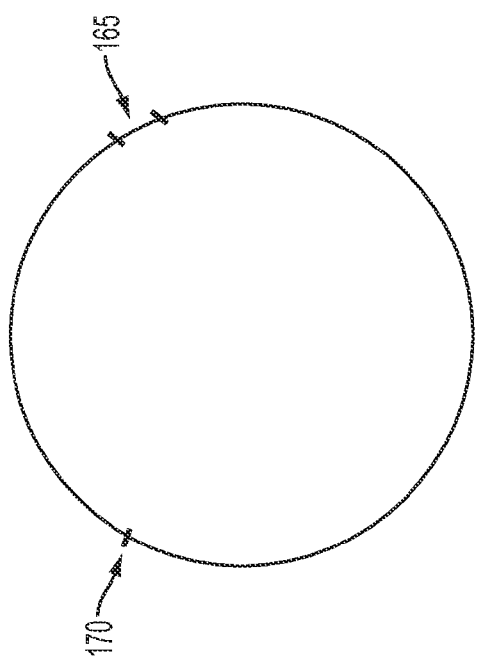
FIG. 3A
FIG. 3B

EASY OPEN LINERS FOR SOIL SAMPLERS

FIELD OF THE INVENTION

The invention relates to a system and method for an easy-to-open liner for use in connection with soil samplers, including direct push technology, rotary and coring systems. The liner according to the invention is pre-scored by at least one score line, which may comprise an indentation of substantially uniform depth or a series of perforations in the outer surface of the liner, in one or more locations. After removal from the soil sampler, the liner of the invention can easily be opened to expose the contained sample without the need of cutting blades or other sharp objects in accordance with health and safety requirements.

BACKGROUND OF THE INVENTION

Site investigations for environmental remediation operations require the extraction of soil and/or chemical samples for geologic characterization. Direct-push technology (DPT) systems are hydraulically powered machines that use static and/or dynamic percussion force to advance small-diameter sampling tools to retrieve soil samples. A well known DPT system is the Geoprobe® Large Bore (LB) Soil Sampler®.

DPT systems operate by attaching a soil sample tube to a probe rod and driving the sample tube the subsurface using a direct-push probing machine. A removable liner is placed inside the sample tube. The sample is collected in the sample tube, which is then withdrawn from the sub-surface to the surface and the liner containing the sample is removed from the sample tube. Liners may be made from a variety of materials, including clear polyvinylchloride (PVC), unplasticized polyvinylchloride (UPVC), Lexan® or other suitable plastic material.

To recover the sample, the liner must be opened. Cutting tools exist for opening liners. For example, Geoprobe® Systems of Salinas, Kans. sells liner cutters which create two parallel slits along the length of the filled liner. The liner must be secured by a liner holder, also sold by Geoprobe® Systems, or a vise, to use the liner cutter. Often, though, staff cut open the liners by pulling a blade down the surface of the liners towards themselves. This approach has been known to result in cutting injuries to the person and his/her gear.

U.S. Pat. No. 5,606,139 to Wittig, Kejr and Christy titled Soil Sample Probe With Retaining Ring for Holding Core-Catching Structure Within the Probe, the contents of which are herein incorporated by reference in their entirety, discloses a soil probe comprising a removably attached sample tube and a liner positioned in the sample tube for receiving a soil sample. After the sample tube has been filled with the soil sample, it is removed from the ground and the liner with the sample therein is removed from the sample tube. The soil sample can be removed from the liner by forcing the core out of the liner or by simply slitting the liner and peeling it from the core.

SUMMARY OF THE INVENTION

The invention relates to a system and method for an easy-to-open liner for use in connection with soil samplers, including direct push technology systems. The liner according to the invention is pre-scored by one or more score lines comprising an indentation of substantially uniform depth or a series of perforations in the outer surface of the liner in one or more locations on the outer surface of the liner. After being removed from the soil sampler, the liner of the invention can easily be opened to expose the contained sample without the need of cutting blades or other sharp objects. The liner of the invention permits safe and easy opening in accordance with health and safety requirements.

According to one embodiment of the invention, a liner for use in lining sample tubes in soil sampling systems comprises PVC, UPVC, a polycarbonate resin thermoplastic such as Lexan® or other suitable plastic material. The liner is scored with at least one double score line configuration (i.e., two closely spaced parallel lines of scoring from approximately 3 mm to 15 mm apart) to form at least one tear strip. The score lines do not extend through the wall of the liner. The end of the tear strip can be gripped and pulled. The liner may further comprise printed cues indicating the location of the tear strip and the direction to pull the tear strip. Upon pulling, the tear strip separates from the liner in a controlled tear to open the liner and reveal the sample, thus allowing the liner to be opened without the use of cutting blades.

According to another embodiment of the invention, a liner for use in lining sample tubes in soil sampling systems comprises PVC, UPVC, a polycarbonate resin thermoplastic such as Lexan® or other suitable plastic material. The liner is scored with at least one double score line configuration to form at least one tear strip and at least one single score line configuration. The score lines do not extend through the wall of the liner. The end of the tear strip can be gripped and pulled. The liner may further comprise printed cues indicating the location of the tear strip and the direction to pull the tear strip. Upon pulling, the tear strip separates from the liner in a controlled tear to open the liner and reveal the sample, thus allowing the liner to be opened without the use of cutting blades. The liner is flexible in the nature of a hinge in the area of the single score line such that once the liner is opened, it can be unfolded to more fully expose the sample.

Also disclosed is a method of manufacturing a scored liner for use in a lining sample tube in soil sampling systems. A liner is formed by extrusion and one or more cutting tools are positioned along with the die to form scored lines on the wall of the liner. The product is then cooled such that the cooled liner includes the scored lines in the configuration and depth desired by the manufacturer.

In another embodiment, the liner can be a commercially available liner, and may comprise PVC, UPVC, a polycarbonate resin thermoplastic such as Lexan® or other suitable plastic material. The liner is scored with at least one double score line configuration to form at least one tear strip and optionally at least one single score line. The liner may further comprise printed cues indicating the location of the tear strip and the direction to pull the tear strip, and the location of the single score line. The scoring and printing can be performed with laser scoring equipment such that the scored lines do not extend through the wall of the liner.

Further disclosed is a method of using a scored liner in a sample tube in soil sampling systems. A soil sampler is attached to a probe rod and driven into the subsurface using a direct-push probing machine. A liner according to the invention is placed inside a sample tube which is situated inside the sampler. The sample is collected in the sample tube, which is then withdrawn from the sub-surface to the surface and the liner containing the sample is removed from the sample tube. The liner is scored with at least one score line configuration to form at least one tear strip and optionally at least one single score line. The liner may further comprise printed cues indicating the location of the tear strip and the direction to pull the tear strip, and the location of the single score line. The score lines do not extend through the wall of the liner. The end of the tear strip is gripped and pulled. Upon pulling, the tear strip separates from the liner in a controlled tear to open the liner and reveal the sample, thus allowing the liner to be opened without the use of cutting blades. The liner may further be unfolded in the area of the single score line after opening to more fully expose the sample. The liner may further comprise printed cues indicating the location of the tear strip and the direction to pull the tear strip and the location of the single score line.

DESCRIPTION OF THE DRAWINGS

The invention will be described with reference to the accompanying drawings, in which like elements are referenced with like numerals.

FIG. 2b depicts an end view of the embodiment of FIG. 2a.

FIG. 3a depicts a left perspective view of an embodiment of the invention comprising a double score line configuration and a single score line configuration.

FIG. 3b depicts an end view of the embodiment of FIG. 3a.

DETAILED DESCRIPTION OF THE INVENTION

Figure 1A:
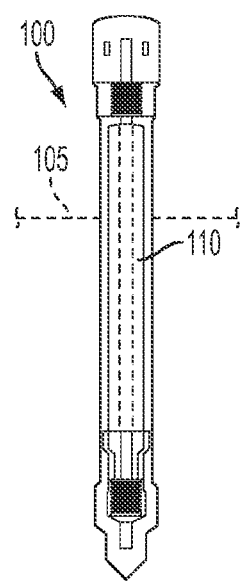
FIGS. 1a-1f depict a typical direct push technology system for sampling sub-surface soil.
Figure 1B:
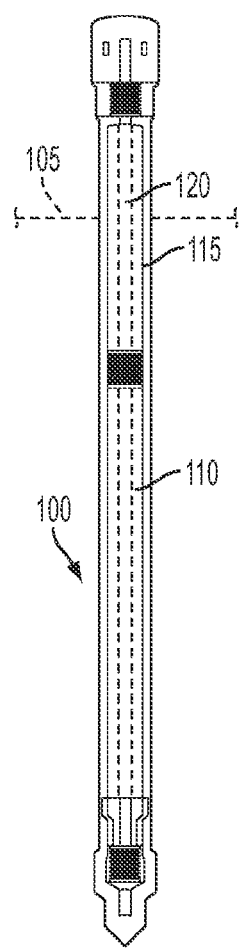
Figure 1C:
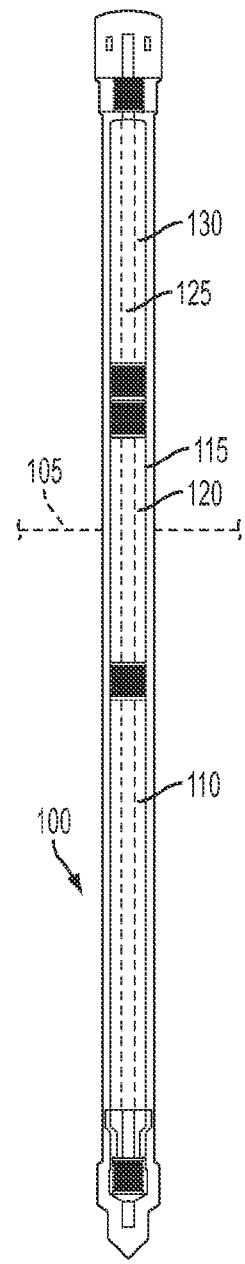
Figure 1D:
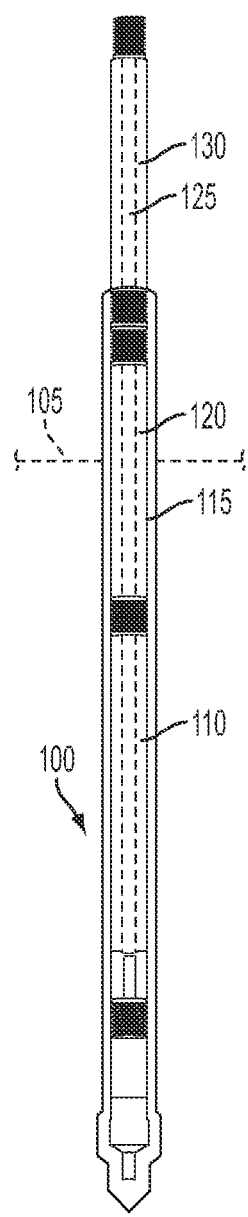
Figure 1E:
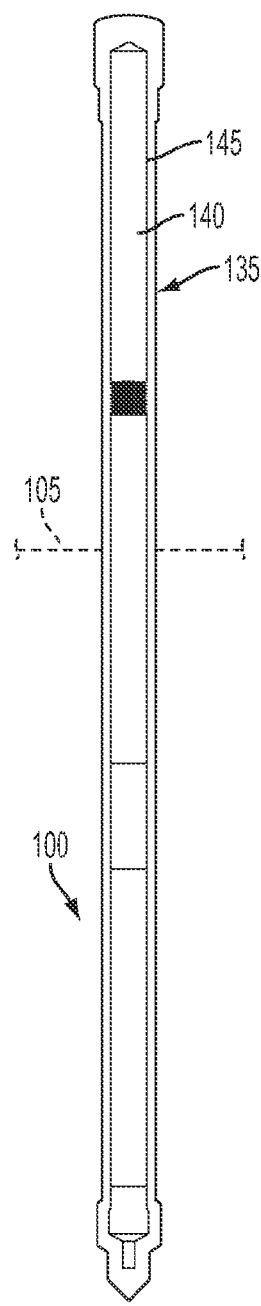
Figure 1F:
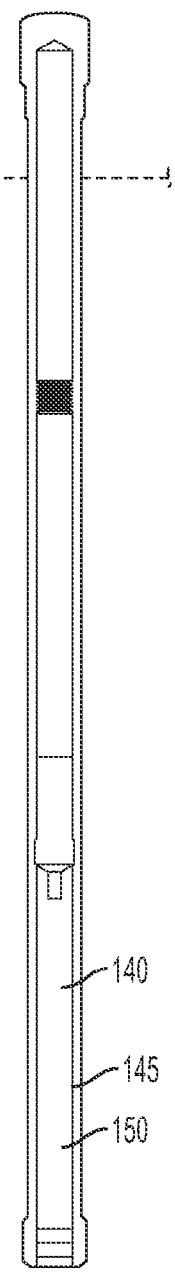

The invention relates to a system and method for an easy-to-open liner for use in connection with soil samplers, including direct push technology systems. The liner according to the invention is pre-scored by one or more score lines comprising an indentation of substantially uniform depth or a series of perforations in the outer surface of the liner in one or more locations. After being removed from the soil sampler, the liner of the invention can easily be opened to expose the contained sample without the need of cutting blades or other sharp objects. The liner of the invention permits the safe and easy opening of liners in accordance with health and safety requirements.

According to one embodiment of the invention, a liner for use in lining sample tubes in soil sampling systems comprises PVC, UPVC, a polycarbonate resin thermoplastic such as Lexan® or other suitable plastic material. The liner is scored with at least one double score line configuration to form at least one tear strip, where the score lines that form a tear strip are approximately 3 mm to 15 mm apart. In one embodiment, the score lines that form a tear strip are approximately 10 mm apart. The score lines do not extend through the wall of the liner. The end of the tear strip can be gripped and pulled. The liner may further comprise printed cues indicating the location of the tear strip and the direction to pull the tear strip. Upon pulling, the tear strip separates from the liner in a controlled tear to open the liner and reveal the sample, thus allowing the liner to be opened without the use of cutting blades. The length of the liner can be sized to accommodate any soil sampling system now known or later developed.

In one embodiment, the liner of the invention comprises two double score line configurations to form two tear strips. In one embodiment, the tear strips are located on the liner on approximately opposite sides from each other.

According to another embodiment of the invention, the liner of the invention comprises at least one double score line configuration to form at least one tear strip and at least one single score line configuration. The tear strip in one embodiment is located at approximately 2 o'clock and the single score line is located at approximately 10 o'clock when viewed from the end of liner.

The score lines do not extend through the wall of the liner. The end of the tear strip can be gripped and pulled. The liner may further comprise printed cues indicating the location of the tear strip and the direction to pull the tear strip. Upon pulling, the tear strip separates from the liner in a controlled tear to open the liner and reveal the sample, thus allowing the liner to be opened without the use of cutting blades. The liner is flexible in the nature of a hinge in the area of the single score line such that once the liner is opened, it can be unfolded to more fully expose the sample.

According to another embodiment of the invention, a liner for use in lining sample tubes in soil sampling systems comprises PVC, UPVC, a polycarbonate resin thermoplastic such as Lexan® or other suitable plastic material. The wall thickness of the liner in one embodiment comprises about 1.2 mm. The depth of the scoring comprises about 0.8 mm. The diameter of the liner may be sized to fit all sample tube sizes used in site investigation ranging from 26 mm to 300 mm, including but not limited to 52.5 mm; 87 mm; 97 mm; and 124 mm.

Also disclosed is a method of manufacturing a scored liner for use in a lining sample tube in soil sampling systems. Raw material in the form of small beads, or resin, is fed into the barrel of an extruder. Additives such as colorants and UV inhibitors can be mixed into the raw material prior to loading into the hopper. The raw material, with additives if desired, are fed into the barrel of the extruder at the back end where it contacts the rotating extruder screw. The screw forces the raw material forward through the barrel which is heated to the desired melt temperature of the molten raw material. There may be heater zones to set up a heating profile for the extruder barrel to gradually increase the temperature of the barrel from the back end where the raw material enters the extruder barrel to the front end of the extruder barrel. Extra heat is caused by the pressure and friction inside the barrel. Cooling fans and/or heat exchangers may be present to reduce the temperature if too much heat is generated.

After passing through the extruder barrel, the molten raw material enters a die at the front of the extruder barrel, which gives the final product its profile shape. One or more cutting tools are positioned along with the die to form the score lines on the outer surface of the extruded soil liner. The product is then cooled, for example by pulling the extrudate through a water bath which may be under vacuum to keep the molten liner from collapsing. The cooled soil liner comprises one or more score lines in the configuration and depth desired by the manufacturer.

In another embodiment, the liner can be a commercially available liner, and may comprise PVC, UPVC, a polycarbonate resin thermoplastic such as Lexan® or other suitable plastic material. The liner is scored with at least one double score line configuration to form at least one tear strip and optionally at least one single score line. The liner may further comprise printed cues indicating the location of the tear strip and the direction to pull the tear strip, and/or the location of the single score line. The scoring and printing can be performed with laser scoring equipment such that the score lines do not extend through the wall of the liner. Scoring may be performed by any method now known or later developed.

Further disclosed is a method of using a scored liner in a sample tube in soil sampling systems. A soil sampler is attached to a probe rod and driven into the subsurface using a direct-push probing machine. A liner according to the invention is placed inside a sample tube which is situated inside the sampler. A soil sample is collected in the sample tube, which is then withdrawn from the sub-surface to the surface and the liner containing the sample is removed from the sample tube. The liner is pre-scored with at least one double score line configuration to form at least one tear strip and optionally at least one single score line. The liner may further comprise printed cues indicating the location of the tear strip and the direction to pull the tear strip, and the location of the single score line. The score lines do not extend through the wall of the liner. The end of the tear strip is gripped and pulled. Upon pulling, the tear strip separates from the liner in a controlled tear to open the liner and reveal the sample, thus allowing the liner to be opened without the use of cutting blades. The liner may further be unfolded in the area of the single score line after opening to more fully expose the sample.

If the liner comprises two double score line configurations, both tear strips may be opened to fully open up the lining to reveal the sample.

FIGS. 1a-1f depict a typical direct push technology system for sampling sub-surface soil. At FIG. 1a, a soil sampler 100 having center rod 110 is driven into the ground 105 to a first position. At FIG. 1b, a probe 115 and center rod 120 are added to soil sampler 100 and soil sampler 100 is advanced further into ground 105 to a second position. At FIG. 1c, an additional probe 125 and center rod 130 are added to soil sampler 100 and soil sampler 100 is advanced further into ground 105 to the desired sampling position. Center rods 110, 120 and 130 are connected. At FIG. 1d, center rods 110, 120 and 130 are removed. At FIG. 1e, probe rod 135 comprising sample tube 140 is inserted into soil sampler 100. Sample tube 140 is lined with removable liner 145. At FIG. 1f, sample tube 140 is advanced further into ground 105 and sample 150 is collected in liner 145. Sample tube 140 is removed with sample 150 inside liner 145.

Figure 2A:
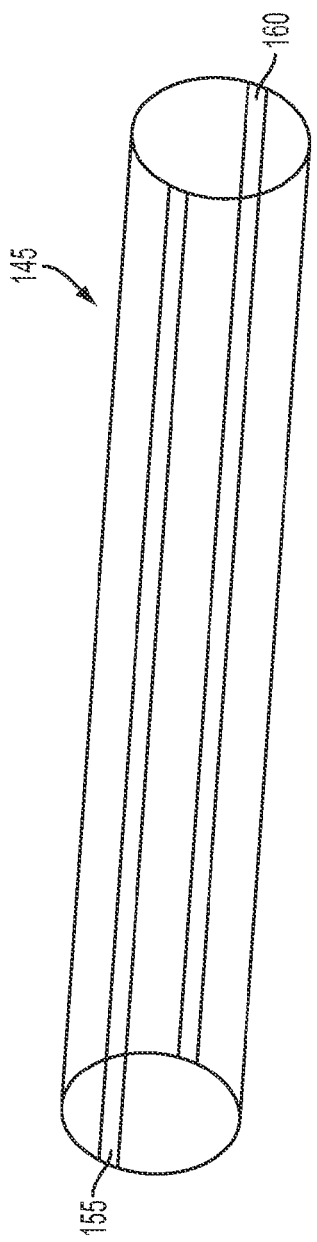
FIG. 2a depicts a left perspective view of an embodiment of the invention comprising two double score line configurations.

FIG. 2a depicts a left perspective view of an embodiment of the invention comprising two double score line configurations. Liner 145 comprises double score line configurations 155 and 160. Double score line configurations 155 and 160 comprise tear strips.

Figure 2B:
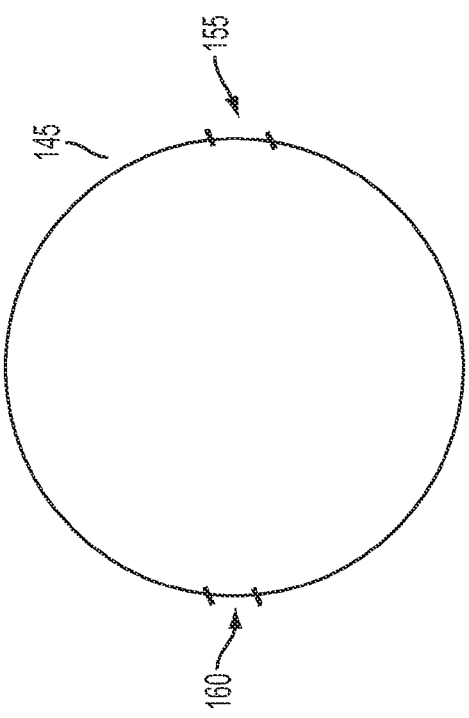

FIG. 2b depicts an end view of the embodiment of FIG. 2a. Tear strips comprising double score line configurations 155 and 160 are located approximately on opposite sides of liner 145.

FIG. 3a depicts a left perspective view of an embodiment of the invention comprising a double score line configuration and a single score line configuration. Liner 145 comprises double score line configuration 165 and single score line configuration 170. Double score line configuration 165 comprises a tear strip.

FIG. 3b depicts an end view of the embodiment of FIG. 3a. Tear strip comprising double score line configuration 165 is located approximately at the 2 o'clock position and single score line 170 is located approximately at the 10 o'clock position when viewed from the end of liner 145.

In another embodiment, the liner may comprise one or more single score lines. The liners may be cut open using cutting blades along the single score line(s). Although this embodiment requires the use of cutting blades, the presence of the score line(s) greatly reduces the force that must be used to open the liner.

The foregoing embodiments have been presented for the purpose of illustration and description only and are not to be construed as limiting the scope of the invention in any way.

What is claimed is:

1. A liner for a soil sampler system, comprising:
   an annular tube comprising a length, an outer surface and an inner surface, wherein the thickness of the annular tube is defined by the distance between the outer surface and the inner surface; and
   a first tear strip, wherein the first tear strip comprises two substantially parallel score line configurations on the outer surface, wherein each score line comprises an indentation of substantially uniform depth or a series of perforations into the thickness of the annular tube wherein the depth of the score line comprising the score line configuration is less than the thickness of the annular tube, wherein at least one score line is configured along the entire length of the annular tube;
   wherein the liner is configured for insertion into a sample tube of a direct push technology system for sampling sub-surface soil,
   wherein further the interior of the annular tube is configured to contain a soil sample.

2. The liner for a soil sampler system of claim 1, wherein the two score lines of the first tear strip are located at a distance of approximately 3 mm to 15 mm apart.

3. The liner for a soil sampler system of claim 2, wherein the two score lines of the first tear strip are located at a distance of approximately 10 mm apart.

4. The liner for a soil sampler system of claim 3, further comprising printing to identify the location of the score line configurations.

5. The liner for a soil sampler system of claim 1, further comprising a second tear strip.

6. The liner for a soil sampler system of claim 5, wherein the two score lines of the second tear strip are located at a distance of approximately 3 mm to 15 mm apart.

7. The liner for a soil sampler system of claim 6, wherein the two score lines of the second tear strip are located at a distance of approximately 10 mm apart.

8. The liner for a soil sampler system of claim 7, wherein the first tear strip and the second tear strip are configured approximately on opposing sides of the annular tube.

9. The liner for a soil sampler system of claim 1, further comprising a third score line configuration.

10. The liner for a soil sampler system of claim 9, wherein the first tear strip and the third score line configuration are configured approximately 120° apart on the annular tube.

11. The liner for a soil sampler system of claim 1, wherein the annular tube comprises polyvinylchloride, unplasticized polyvinylchloride or polycarbonate resin thermoplastic.

12. The liner for a soil sampler system of claim 11, wherein the thickness of the annular tube is approximately 1.2 mm.

13. The liner for a soil sampler system of claim 12, wherein the depth of the score line configurations is approximately 0.8 mm.

14. A method of opening a liner for a soil sampler system comprising:
   inserting a liner into a sample tube into a sampler of a direct push soil sampling system;
   driving the sampler into the sub-surface;
   collecting a soil sample in the interior of the liner;
   withdrawing the sampler from the sub-surface;
   removing the liner containing the soil sample from the sample tube; and
   opening the liner,
   wherein the liner comprises an annular tube comprising a length, an outer surface and an inner surface, wherein the thickness of the annular tube is defined by the distance between the outer surface and the inner surface; and
   wherein the liner comprises a first tear strip and a second tear strip, wherein each of the first tear strip and the second tear strip comprises two substantially parallel score line configurations on the outer surface, wherein the first tear strip and the second tear strip are configured approximately on opposing sides of the annular tube, wherein each score line configuration comprises an indentation of substantially uniform depth or a series of perforations into the thickness of the annular tube into the thickness of the annular tube, wherein the depth of the score line configuration is less than the thickness of the annular tube;

wherein opening the liner comprises opening the liner along at least one of the score line configurations.

15. The method of claim 14, wherein the liner comprises a first tear strip and a third score line configuration, wherein the first tear strip and the third score line configuration are configured approximately 120° apart on the annular tube.

16. The method of claim 14, wherein the two substantially parallel score line configurations on the outer surface are at a distance of approximately 10 mm apart.

* * * * *